(12) United States Patent
Traversaz (10) Patent No.: US 8,328,763 B2
(45) Date of Patent: Dec. 11, 2012

(54) CLAMP FOR A FLEXIBLE TUBE, PUMP PROVIDED WITH MEANS FOR OPENING SUCH A CLAMP, AND INFUSION KIT PROVIDED WITH SUCH A CLAMP

(75) Inventor: Philippe Traversaz, Saint-Blaise du Buis (FR)

(73) Assignee: Fresenius Vial SAS, Brezins (FR)

( * ) Notice: Subject to any disclaimer, the term of this patent is extended or adjusted under 35 U.S.C. 154(b) by 0 days.

(21) Appl. No.: 12/676,498

(22) PCT Filed: Aug. 27, 2008

(86) PCT No.: PCT/EP2008/061252
§ 371 (c)(1),
(2), (4) Date: Jun. 14, 2010

(87) PCT Pub. No.: WO2009/030625
PCT Pub. Date: Mar. 12, 2009

(65) Prior Publication Data
US 2010/0268161 A1    Oct. 21, 2010

(30) Foreign Application Priority Data
Sep. 4, 2007 (FR) ..................................... 07 57337

(51) Int. Cl.
*A61M 5/178* (2006.01)
(52) U.S. Cl. ................... 604/167.01; 604/151; 604/153; 604/250; 604/412; 251/4; 251/9; 251/117
(58) Field of Classification Search .................. 251/4, 9, 251/10, 117; 604/151, 153, 167.01, 250, 604/412
See application file for complete search history.

(56) References Cited

U.S. PATENT DOCUMENTS
350,850 A * 10/1886 Tatum .............................. 251/10
(Continued)

FOREIGN PATENT DOCUMENTS
EP    0186509 A2    7/1986
(Continued)

OTHER PUBLICATIONS
International Search Report of PCT/EP2008/061252, mailing date of Dec. 15, 2008.

*Primary Examiner* — Nicholas Lucchesi
*Assistant Examiner* — Scott Medway
(74) *Attorney, Agent, or Firm* — Westerman, Hattori, Daniels & Adrian, LLP (57) ABSTRACT

The invention relates to a clamp (10) for a flexible tube, in particular an infusion tube, composed of a substantially U-shaped plastic band, the free end (111) of the first branch (11') of the U being bent over, so as to form the head (11) of the clamp, to the free end (121) of the second branch, called the back (12), in such a way that, in the closed position, the free end (121) of the back (12) is situated resting under the free end (111) of the head (11), whereas, in the opened position, the free end (121) of the back (12) is situated at a distance above the free end (111) of the head (11), the clamp having a pair of openings (114, 134) to allow a flexible tube to extend through the clamp and be supported by the latter, and two opposite projections (113, 123) for obturating the flexible tube by compressing it when the clamp is in the closed position. The invention also relates to a pump provided with means for opening a clamp according to the invention, to an infusion kit provided with a clamp according to the invention, and to a combination of a pump according to the invention and an infusion kit according to the invention. According to the invention, locking means (112, 122) are provided in order to ensure that the head end (111) does not move away from the back end (121) when the clamp (10) is in the closed position.

18 Claims, 11 Drawing Sheets

U.S. PATENT DOCUMENTS

| | | | | |
|---|---|---|---|---|
| 1,361,770 | A * | 12/1920 | O'Connor | 251/10 |
| 2,682,874 | A * | 7/1954 | Hickey | 604/412 |
| 2,722,932 | A * | 11/1955 | Hickey | 604/412 |
| 3,822,052 | A * | 7/1974 | Lange | 251/10 |
| 3,942,228 | A * | 3/1976 | Buckman et al. | 251/4 |
| 4,053,135 | A * | 10/1977 | Saliaris | 251/10 |
| 4,235,412 | A * | 11/1980 | Rath et al. | 251/10 |
| 4,278,085 | A * | 7/1981 | Shim | 604/500 |
| 4,429,852 | A * | 2/1984 | Tersteegen et al. | 251/9 |
| 4,588,160 | A * | 5/1986 | Flynn et al. | 251/10 |
| 4,589,626 | A * | 5/1986 | Kurtz et al. | 251/10 |
| 4,643,389 | A | 2/1987 | Elson et al. | |
| 4,673,161 | A * | 6/1987 | Flynn et al. | 251/10 |
| 4,802,650 | A * | 2/1989 | Stricker | 251/117 |
| 5,035,399 | A * | 7/1991 | Rantanen-Lee | 251/10 |
| 5,090,877 | A * | 2/1992 | D'Silva | 417/474 |
| 5,211,548 | A * | 5/1993 | Okada | 417/474 |
| 5,219,327 | A | 6/1993 | Okada | 604/34 |
| 5,423,769 | A * | 6/1995 | Jonkman et al. | 604/250 |
| 5,437,642 | A * | 8/1995 | Thill et al. | 604/153 |
| 5,951,519 | A | 9/1999 | Utterberg | |
| D427,307 | S * | 6/2000 | Guala et al. | D24/129 |
| 6,089,527 | A * | 7/2000 | Utterberg | 251/4 |
| D431,650 | S * | 10/2000 | Guala et al. | D24/129 |
| 6,161,812 | A * | 12/2000 | Guala et al. | 251/10 |
| 6,482,190 | B1 * | 11/2002 | Genese et al. | 604/327 |
| 6,503,221 | B1 * | 1/2003 | Briggs et al. | 604/67 |
| 6,644,618 | B1 * | 11/2003 | Balbo | 251/10 |
| D590,061 | S * | 4/2009 | Stephens | D24/129 |
| 7,560,686 | B2 * | 7/2009 | Bisch et al. | 250/231.1 |
| 7,611,498 | B2 * | 11/2009 | Hasler | 604/250 |
| D637,712 | S * | 5/2011 | Chau et al. | D24/129 |
| D638,121 | S * | 5/2011 | Villasana | D24/128 |
| 7,954,210 | B2 * | 6/2011 | Ruffing | 24/489 |
| 2002/0169423 | A1 | 11/2002 | Zoltan et al. | |
| 2005/0020978 | A1 | 1/2005 | Vollenweider | |
| 2005/0215975 | A1 | 9/2005 | Mathias et al. | |
| 2006/0079849 | A1 | 4/2006 | Zoltan et al. | |
| 2006/0081797 | A1 | 4/2006 | Zerfas | |
| 2007/0252096 | A1 | 11/2007 | Zerfas | |
| 2008/0294122 | A1 * | 11/2008 | Chesnin et al. | 604/250 |
| 2010/0096570 | A1 * | 4/2010 | Kashmirian et al. | 251/9 |

FOREIGN PATENT DOCUMENTS

| | | |
|---|---|---|
| EP | 1218055 A1 | 7/2002 |
| WO | 98/48872 A1 | 11/1998 |
| WO | 00/44434 A1 | 8/2000 |
| WO | 03/041787 A2 | 5/2003 |
| WO | 03/063945 A1 | 8/2003 |

* cited by examiner

CLAMP FOR A FLEXIBLE TUBE, PUMP PROVIDED WITH MEANS FOR OPENING SUCH A CLAMP, AND INFUSION KIT PROVIDED WITH SUCH A CLAMP

The invention relates to a clamp for a flexible tube, in particular, a tube for perfusion, made of a substantially U-shaped band of plastic material, with the free end of the first branch of the U bent toward the free end of the second branch, called the back, to form the head of the clamp, so that in the closed position, the free end of the back is supported under the free end of the head, whereas in the open position, the free end of the back is above the free end of the head at a distance, the clamp having a pair of openings to accommodate a flexible tube going through the clamp and supported by it, and two opposite protrusions to seal off the flexible tube by compressing it when the clamp is in the closed position. The invention also relates to a pump equipped with means for opening and closing a clamp according to the invention, a perfusion set equipped with a clamp according to the invention, and a combination of a pump according to the invention and a perfusion set according to the invention.

Document EP 1218055 A1 describes such a clamp, commonly called a snail clamp. It also describes such a pump for perfusion, such a perfusion set, and such a combination of a pump for perfusion and a perfusion set. The pump described in this document is equipped with means for closing the clamp and means for opening the clamp that when pressure is exerted by a perfusion pump actuation element for opening or closing the clamp. The means for closing the clamp are in the shape of a bulge formed on the outside face of the end, over which at least part of a tilting lever of the perfusion pump rolls.

Document WO 00/44434 A1 also describes a clamp for flexible tubing according to the preamble of claim 1. This clamp has openings for the flexible tubing that extend axially through the side edge of the clamp, and which are each positioned near a portion of band that is narrow relative to the rest of the band. In order to reinforce the narrow band portion, the document proposes making at least one of the narrow parts of the band extend laterally outward past the second side edge of the rest of the band.

The clamp in document EP 1218055 A1, which can be closed and opened by an actuation means of the perfusion pump, has considerably increased the operating safety of such devices.

However, in the closed position, these snail clamps can be opened inadvertently by pushing on the free end of the head, which end keeps the other end of the clamp in the tightened position.

A purpose of the invention is to further improve operating safety and facilitate the operations involved in setting up for perfusion.

This purpose is achieved for a clamp according to the preamble in that locking means are provided so as to prevent the free end of the head from moving away from the free end of the back when clamp is in the closed position.

This can be easily achieved, for example, when the locking means consist of a tab located on the head end and a recess located on the back end, the tab and the recess being arranged so that in the closed position of the clamp, the tab goes into the recess, with an actuation element preferably provided on the end of the head. Once the tab is inside the recess, it is impossible to open the clamp just by pressing on the end of the head, as is the case with the clamps known in the prior art. That is, in order to move the head end away so as to release the back end, one must also press on the back to get the tab out of the recess, as well as move the head end away. This dual movement is easy to carry out per se, but requires coordinating these two movements, so that it is practically out of the question for the clamp to be unintentionally opened. Simply pressing on the back of the clamp makes the tab come out of the recess, but it goes back into the recess when pressure stops if it has not been moved away. Thus the clamp remains closed.

According to the invention, an insert is provided in one of the openings of the clamp to receive the end of the flexible tube, the insert being integral with the clamp. This insert is preferably made of hard plastic material and is cylindrical in shape. Since it is integral with the clamp, it cannot be displaced in the direction of the tube. It is preferably inserted into the opening located in the bottom of the U of the clamp. It protects the end of the flexible tube coming out of the clamp and through this opening.

In a development of the invention, the insert is equipped with an end fitting for attaching another flexible tube. The insert can thus serve as a connector between two flexible tubes, and optionally between two flexible tubes with different characteristics, such as a very flexible tube going through a finger pump and another, less flexible one that is not subject to the same stresses.

A further development of the invention consists in equipping the insert with a groove on its outer circumference, which receives the two opposite edges of the clamp opening, which can itself be provided with a cut-out to accommodate the insert. The insert is fitted into the clamp to hold it in place. If the clamp opening has the shape of a slot extending approximately 180° in the bottom of the U of the clamp, then even though the guide element is held in the clamp, it can tilt in this slot around an axis passing through the cut-out. If it is cylindrical in shape, it can also pivot.

According to the invention, a longitudinal groove is provided on the outer face of the back of the clamp. This groove in the middle of the back of the clamp makes it possible to guide an actuator cam placed on a tilting lever of the perfusion pump when the clamp is opened or closed.

The invention also relates to a pump for perfusion equipped with a door that can be opened and closed so as to place or take out a flexible tube equipped with a clamp according to the invention, the pump being equipped with means for opening or closing a clamp located on the inside, means comprising a pivoting lever equipped with at least one head cam to move the end of the head away from the end of the back. According to the invention, the lever is equipped with means for unlocking the clamp locking means. It is additionally preferable that the pump be equipped with means for closing the clamp when the door is opened to eliminate any risk of free flow when the tube is withdrawn from the pump.

This is easily achieved, for example, when the unlocking means consist of at least a back cam, the head cam and the back cam being disposed on the lever pivot axis so that when the lever is actuated to open the clamp, first the back cam presses on the back of the clamp until the clamp locking means are unlocked and it holds the clamp in this position, then the head cam moves the free end of the head far enough away to leave room for the end of the back to go through, after which the back cam releases the pressure on the back of the clamp, and lastly, the head cam releases the end of the head. The lever thus makes it possible to open or close the clamp, opening it by exerting pressure on the back of the clamp and then moving the other end away from it so that the two ends move away from one another. This way, not only is the tab taken out of the recess, but in addition, the tab is out of line with respect to the recess so that it cannot fall back inside. In order to close the clamp, simply pressing on the back of the clamp is sufficient to make the clamp tab go back in the recess. Of course, it is also possible to carry out the above-described opening movement in reverse.

In a variant of the invention, the lever is placed in the door of the pump. In order to use the lever and to open and close the clamp as well as open and close the door, it can be additionally equipped with a hook able to cooperate with a roller located on the pump housing in order to keep the door closed.

In a variant of the invention, its operation can be handled by a motorized system that is synchronous with door opening and closing.

In a preferred embodiment of the invention, the door is equipped with a return element that serves to move the hook into the closed position as soon as the clamp opening and closing means have placed the clamp in the open position. This way, one can be sure that the door is truly closed as soon as the lever is released after the door closes (and thus that the clamp is open). Likewise, in case the lever is raised unintentionally without any intention of opening the door, the lever will be returned to the closed position without triggering the clamp to close as long as a certain pivot point has not been reached.

It is also useful to provide a support on the pump housing for snapping in the clamp insert.

The invention also relates to a perfusion set made up of a flexible tube going through a clamp according to the invention.

It is advantageous in this context to connect two flexible tubes with different characteristics to one another by means of an insert that is integral with the clamp.

Lastly, the invention relates to a combination of a pump for perfusion according to the invention and a flexible tube set for perfusion according to the invention.

The invention is described below using examples of embodiments presented in the figures, which show:

FIG. 2 the clamp in FIG. 1, (a) in the closed position, (d) in the open position, and (b, c) in intermediate positions;

FIG. 3 perspective views of a pump according to the invention with (a) the door closed and (b) the door open;

FIG. 6 a representation of the pump when the lever is in the open position (a) in cross-section through the door closing means and (b) clamp unlocking means;

FIG. 11 views (a) before and (b) after snapping the insert into its support.

Figure 1:
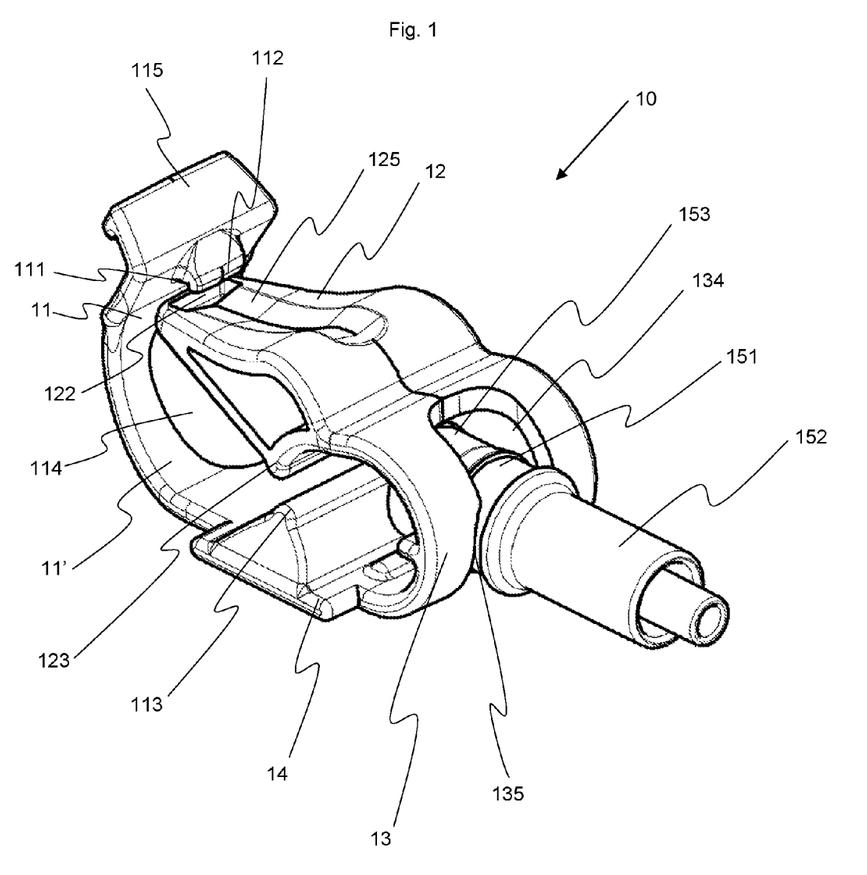
FIG. 1 a clamp according to the invention, seen in perspective.

FIG. 1 shows a clamp (10) for a flexible tube that can be opened and closed again and again. This clamp, a snail-type clamp, consists of a generally U-shaped band of plastic material. The lower branch (11') of the U has its end bent upward toward the upper branch (12). The free end (111) of the lower branch (11) is extended by an actuation element (115). The upper branch (12) is called the back of the clamp, whereas the bent part (11) of the lower branch is called the head of the clamp. With no external stress, the free end (121) of the back (12) of the clamp is above the free end (111) of the head (11). In the closed position, the free end (121) of the back (12) is under the free end (111) of the head (11) and pushing against it due to the spring action of the bow that forms the bottom (13) of the U.

The lower branch (11') and the back (12) are each equipped with a protrusion (113, 123) that, when the clamp is closed, serve to clamp the tube going through it. Two openings (134, 114) have been made in the bottom (13) and in the head (11) of the clamp to allow the tube to pass through the clamp.

Figure 2A:
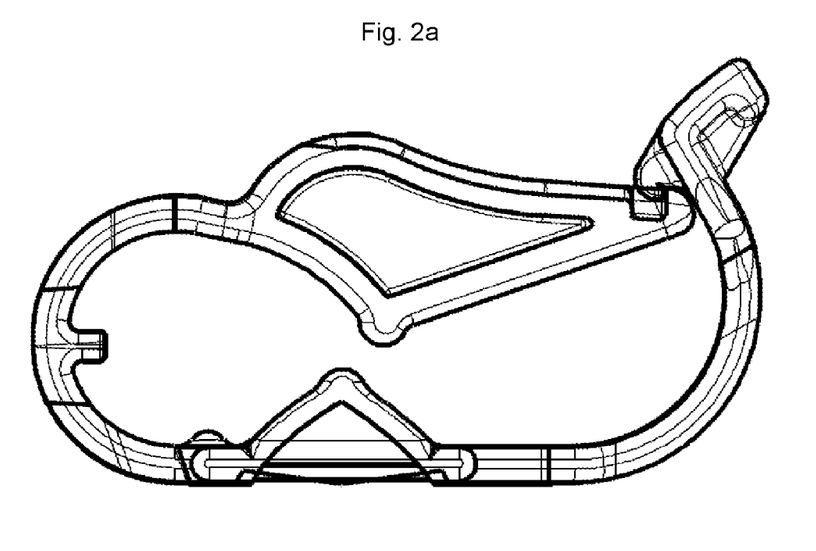

In order to open prior art clamps, pressure must be exerted on the head in order to move it away from the free end of the back, the pressure being applied in a direction substantially parallel to the surface where the two ends overlap. The clamp (10) of the invention is distinguished from those of the state of the art by the presence of locking means that prevent the free end (111) of the head (11) from unintentionally being separated from the free end (121) of the back (12) when the clamp is in the closed position. These locking means are made up of a tab (112), firstly, located on the free end (111) of the head (11) and a recess (122), secondly, located on the free end (121) of the back (12). As seen in the Figures, these locking means can also be seen as a recess located on the free end of the head and a tab located on the free end of the back. The tab (112) and the recess (122) are disposed on their respective branches in such a way that in the closed position of the clamp, the tab (112) is inside the recess (122). When the clamp is in the closed position, the tab (112) and the recess (122) come up against one another if one tries to separate the head end (111) from the back end (121) in a movement substantially perpendicular to the direction the tab penetrates. In other words, the abutting surfaces of the tab (112) and the recess (122) are substantially perpendicular to the surface along which the two ends (111, 121) overlap. The clamp is thus locked. FIG. 2a illustrates this situation.

Figure 2B:
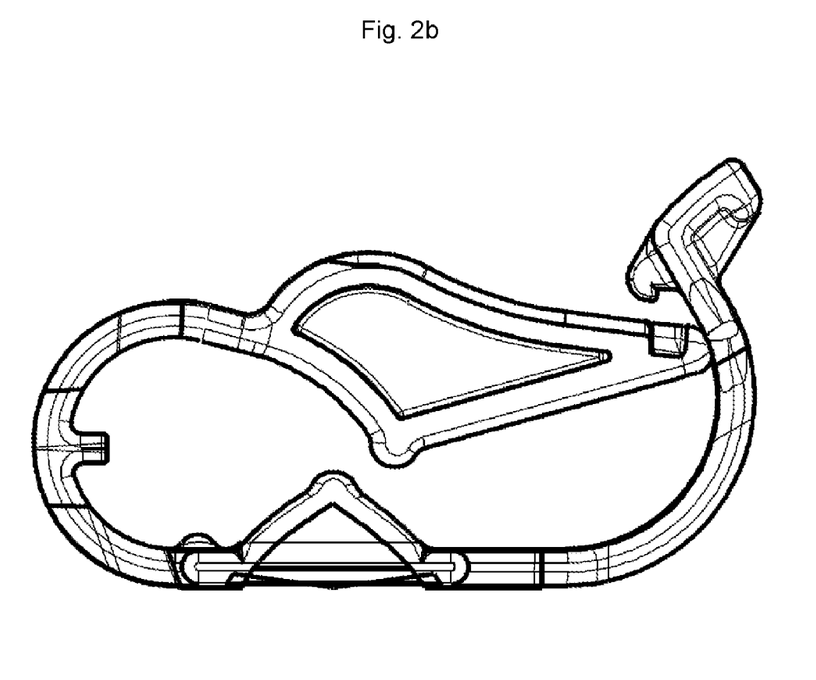

To open the clamp, pressure must be applied first to the back (12) to move it toward the center of the clamp so as to get the tab (112) to come out of the recess (122). FIG. 2b illustrates this position. If this pressure is stopped, the back rises back up due to the spring action of the bow that forms the bottom (13) of the U, the tab goes back into the recess, and the clamp remains closed. As shown on FIG. 2b, the protrusions are staggered along a direction from one of the orifices to the other in the closed position of the clamp, so that the back can be pushed toward the bottom past the closed position of the clamp.

Figure 2C:
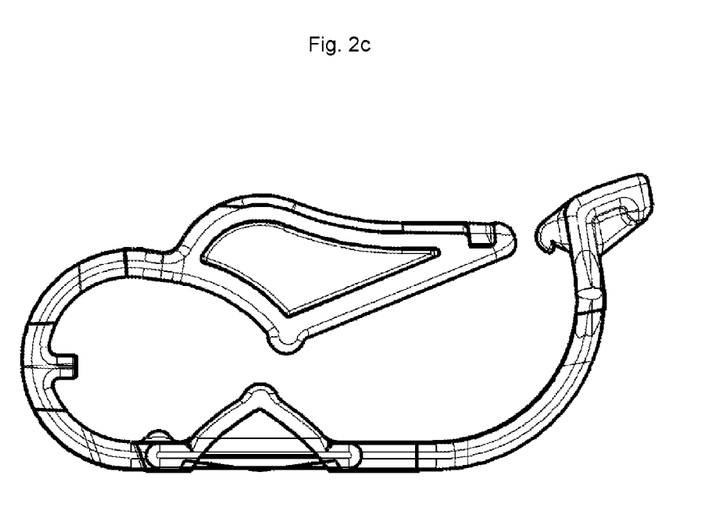

When the back is pushed far enough toward the inside of the clamp, past the closed position of the clamp, so that the tab (112) is outside the recess (122), pressure may be applied to the free end (111) of the head (11) to move it away from the free end (121) of the back until the latter can move past in front of the free end (111) of the head (11) without being blocked. The clamp is in the position illustrated in FIG. 2c.

Figure 2D:
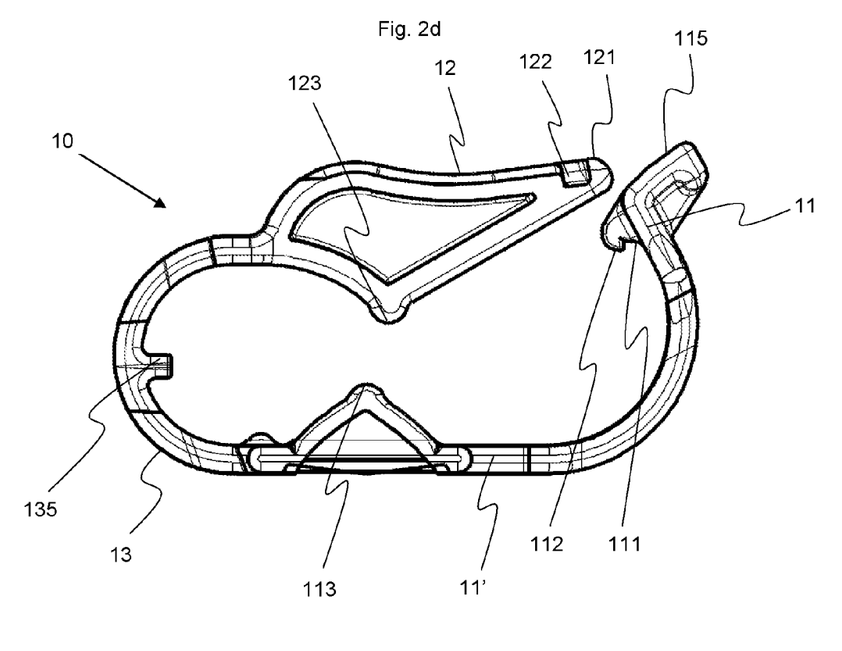
Figure 3A:
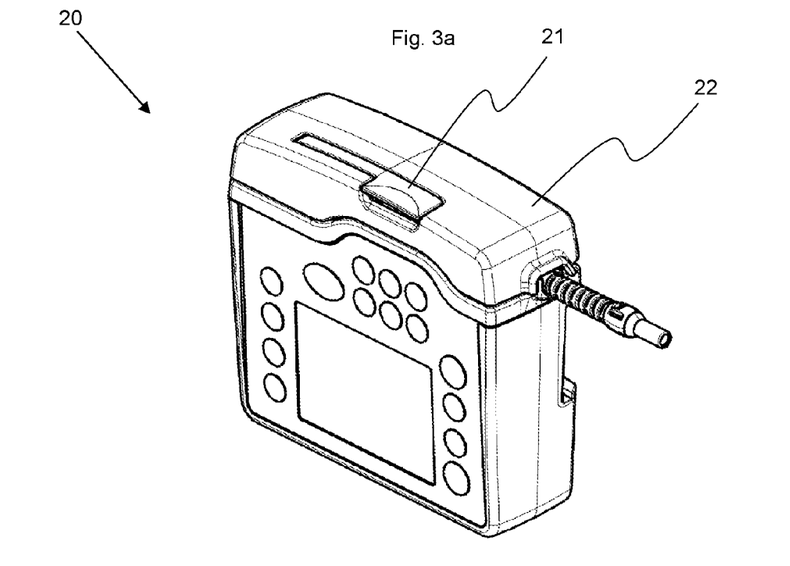
Figure 3B:
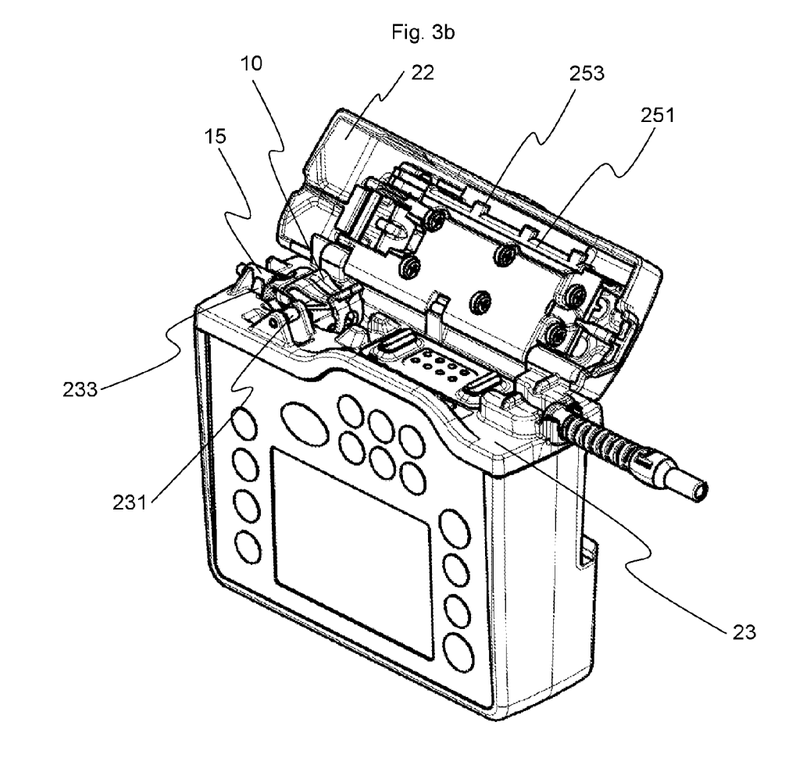

While keeping the head end (111) pulled away, the pressure being applied on the back (12) is removed. Due to the spring action of the bottom (13) of the clamp, the back (12) moves away from the lower branch (11'), with the end (121) thereof going by in front of the pulled-back end of the head (111). The pressure being applied to move the head end away can now be stopped. The clamp is in the open position shown in FIG. 2d. In this position, the two protrusions (113, 123) are no longer exerting pressure on the tube, and the fluid can flow normally.

With these locking means, in order to open the clamp one must press on the back (12) of the clamp and simultaneously move the head end (111) away as well, in two substantially perpendicular movements. This dual movement is easily accomplished, but because the two movements must be coordinated, this eliminates practically any risk of opening the clamp unintentionally. These two movements do not have to be absolutely perpendicular to one another; they can simply be angled enough to prevent a divergence in force from causing the free end of the back to move toward the center of the clamp without any pressure being exerted on the back. This principle is expressed here with the term "substantially" perpendicular.

To close the clamp (10), one can simply press the back (12) toward the lower branch (11'). The end of the back (121) then slides on the angled actuation element (115) extending from the head end (111) and pushes it far enough away to make itself a space to go through. As soon as the end of the back (121) has gone past the end of the head (111), the latter (111) returns to its initial position and blocks the back (12).

It is also possible to use the same procedure as for opening the clamp, but in reverse.

When the clamp (10) of the invention is placed in a pump, the latter must be equipped with means for unlocking the clamp (10) in order to open it when the door is closed or to close it when the door is opened. This is necessary in order to prevent a free flow when the door (11) opens or closes, and this applies regardless of how far along the door (11) is in closing. Generally speaking, the clamp (10) must be open when the door (22) of the pump (20) is closed, and be closed when the door (22) of the pump (20) is opened. Pumps meant to use snail clamps are thus generally equipped with means for opening the clamp when the pump door is closed, and conversely, for closing the clamp when the door is opened.

Figure 4:
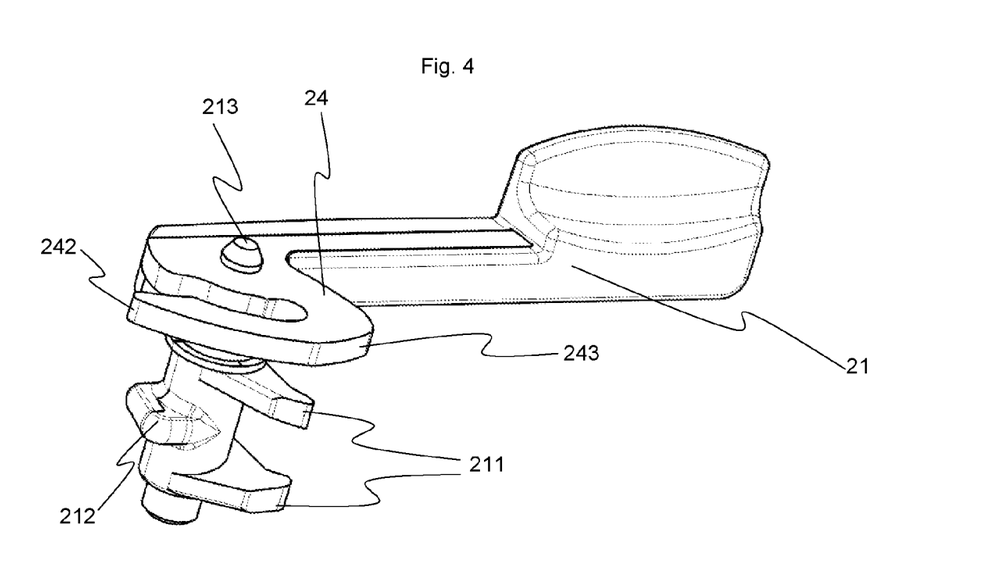
FIG. 4 a perspective view of the lever of the pump according to the invention.

For this purpose, the pump (20) is equipped with a pivoting lever (21), usually placed in the door (22). The lever (21) is equipped with at least one cam on its rotation shaft (213), here, a pair of cams (211), to push the head end (111) away in a movement substantially parallel to the overlap surface between the ends, so as to make room for the end of the back (121) to go through.

In the present case, this pair of head cams (211) cannot push the head end away, because the latter is held against the back end by the tab (112) that is inside the recess (122).

The lever (21) is thus equipped with a second cam (212), called the back cam, for pressing on the back (12) of the clamp in order to make the tab (112) come out of the recess (122) first. The pair of head cams (211) and the back cam (212) are disposed on the lever (21) shaft in such a way that when the lever is closed down against the door (22), the back cam (212) presses on the back (12) first, before the pair of head cams (211) begins to push the head end (111) away.

Figure 5:
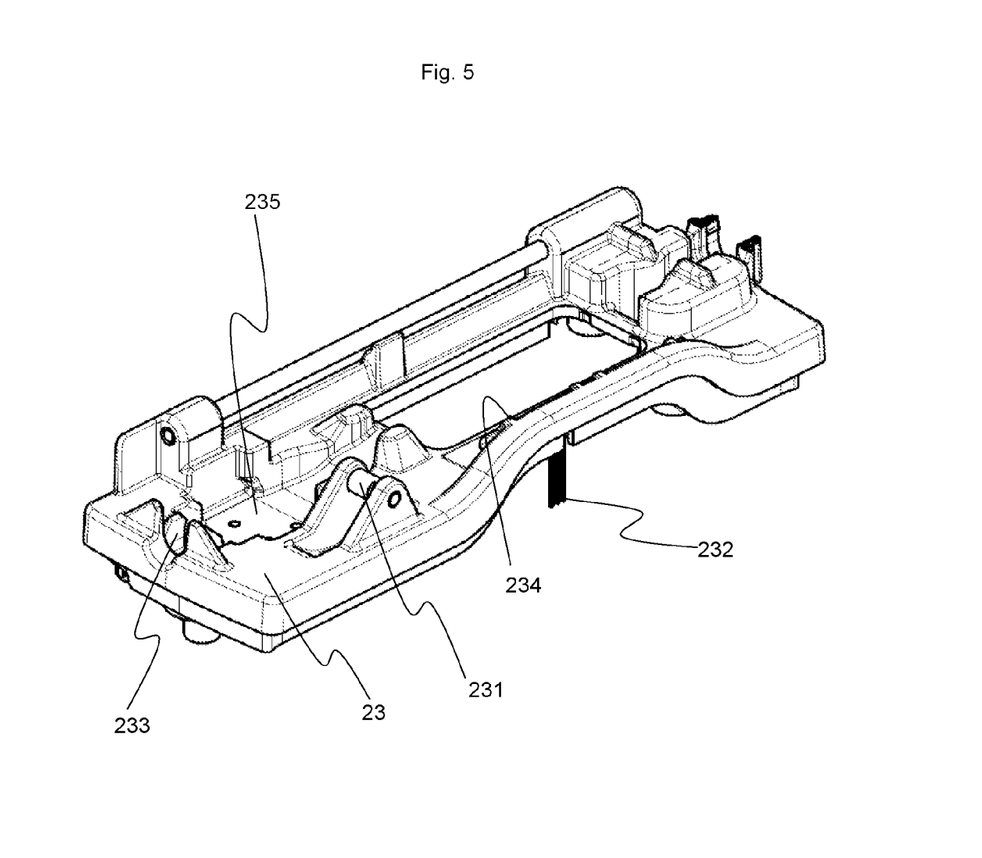
FIG. 5 a view of the part of the pump housing located under the door when the door is closed.

In the example of an embodiment shown here, the lever (21) of the invention is additionally equipped with a hook (24) that cooperates with a pivoting roller (231) placed on the part (23) of the pump located under the door (22) when the latter is closed. The lever (21) thus serves not only to open or close the clamp (10) of the invention placed in the pump, but also to open or close the pump door (22).

FIGS. 6 to 9 show the process of opening the clamp while the door is closing.

If the lever (21) is closed down against the door when the door is open, it cannot be completely closed down against the pump housing (23), because the hook (24) comes up against the roller (231). Thus, the lever (21) must be lifted in order to close the door.

If the lever (21) is upright, the door cannot be closed all the way, either, because the base (241) of the hook comes up against the roller (231) when the door is closed down. At this point, then, the lever (21) must begin to close down against the pump housing (23) in order to be able to lock the door into the closed position. The point (242) of the hook (24) then catches the roller (231) and slides underneath it, pulling the door with it.

When the lever (21) is lowered toward the door (22), the point (242) goes under the roller (231) and, first of all, causes the pivot shaft (213) of the lever (21) to move toward the pump housing (23), pulling the door with it. It also causes the cams (211 and 212) to pivot, and they will be able to act on the clamp (10) to open it once the door is locked.

Figure 6A:
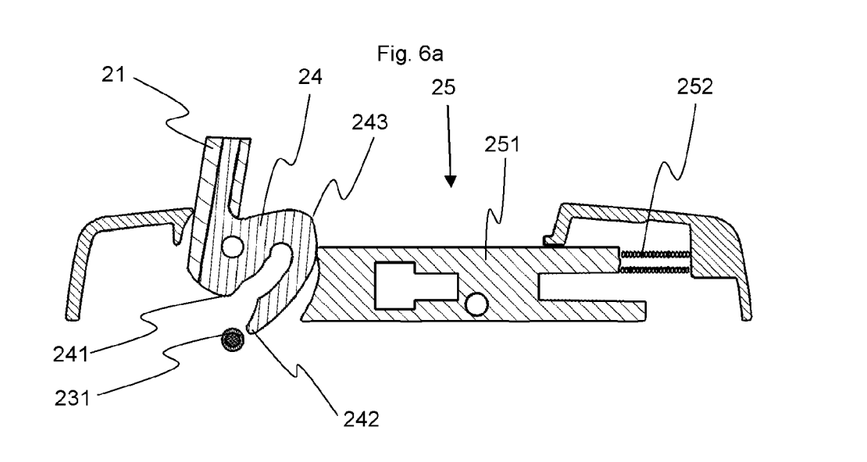
Figure 6B:
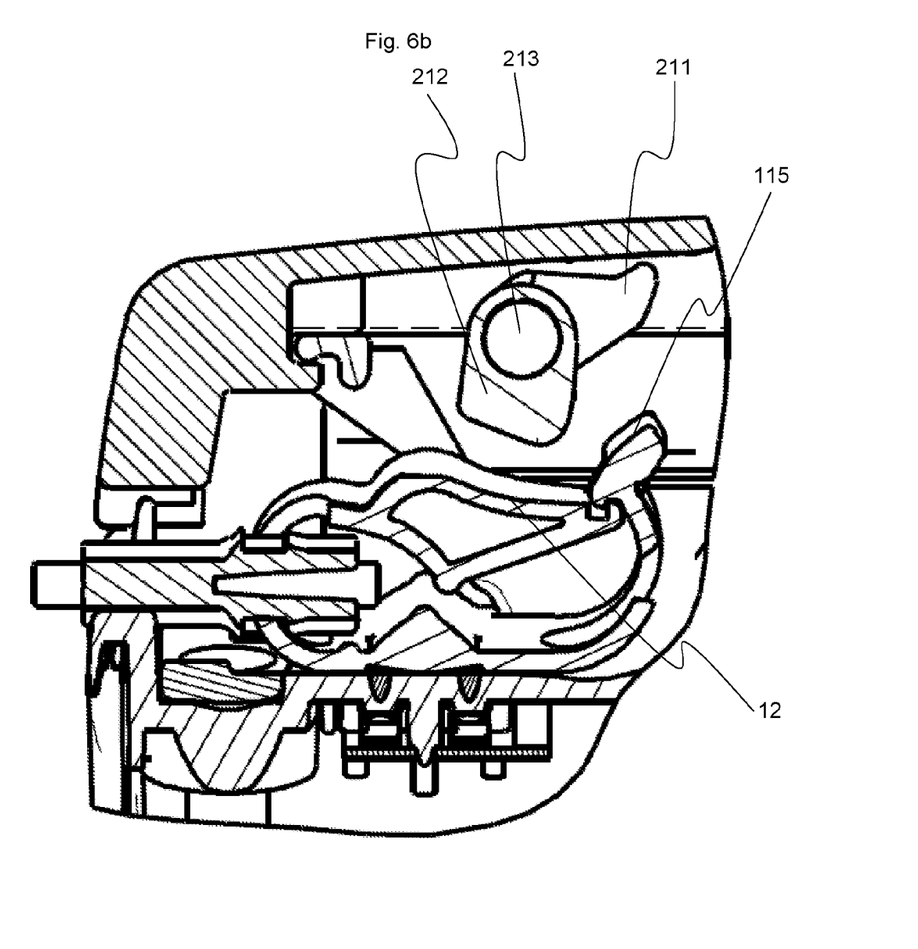
Figure 7A:
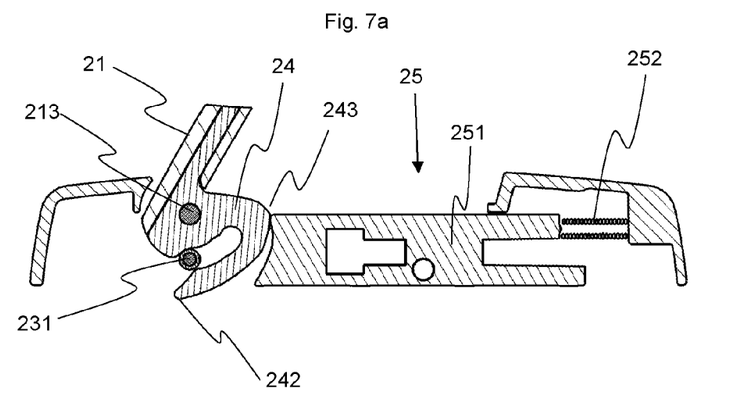
FIGS. 7 and 8 views similar to FIG. 6, with the lever being progressively closed down.
Figure 7B:
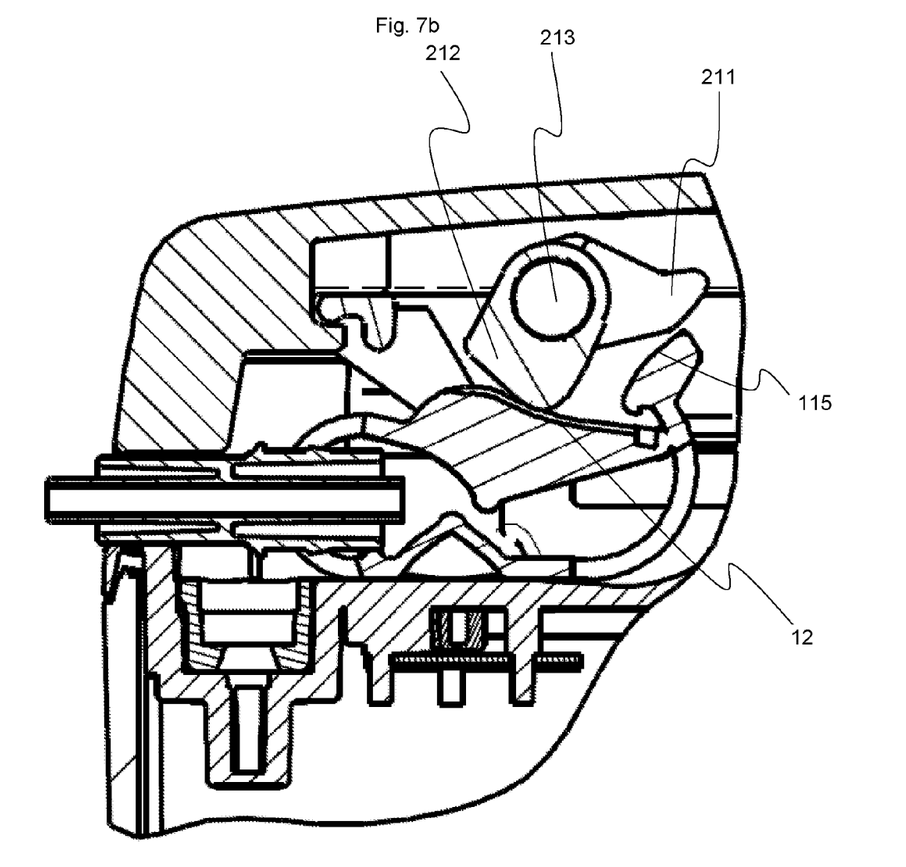

If the clamp (10) is open, the back cam (212) presses on the back (12) of the clamp (10) and causes it to close, firstly. This is the situation shown in FIG. 6.

As the lever (21) continues to lower, the back cam (212) continues to press on the back (12) while pivoting. The back (12) is pushed toward the inside of the clamp (10) past the closed position, and the locking tab (112) comes out of the recess (122). This is the position shown in FIG. 7.

Figure 8A:
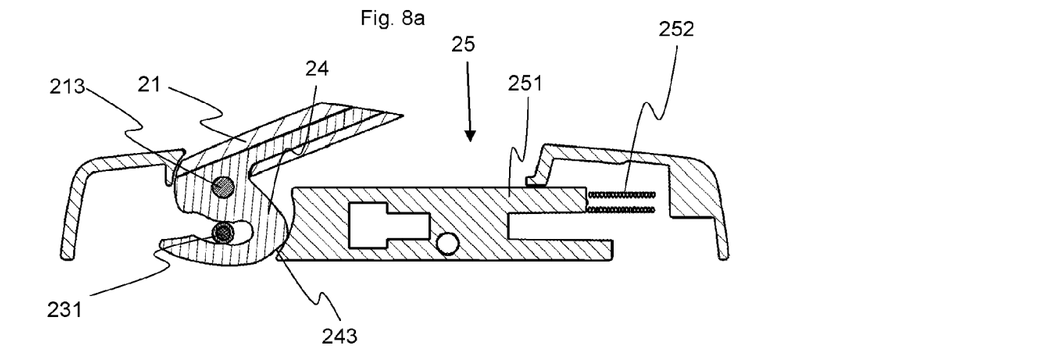
Figure 8B:
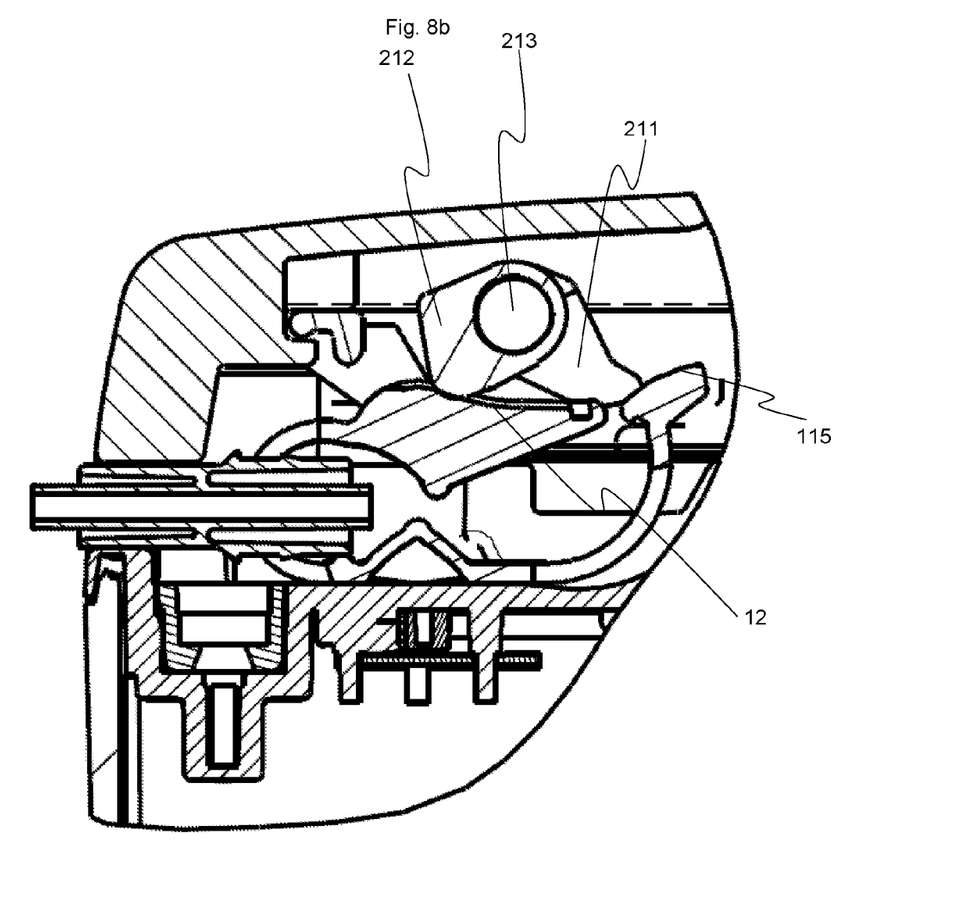

Continuing to pivot the lever (21), the back cam maintains pressure on the back (12) of the clamp (10), slowly decreasing it, while the pair of head cams (211) comes into contact with the actuation element (115) of the head (11) and pushes its free end (111) away from the back end (112). The two ends (111, 121) are thus each in their furthest positions as shown in FIG. 8.

Figure 9A:
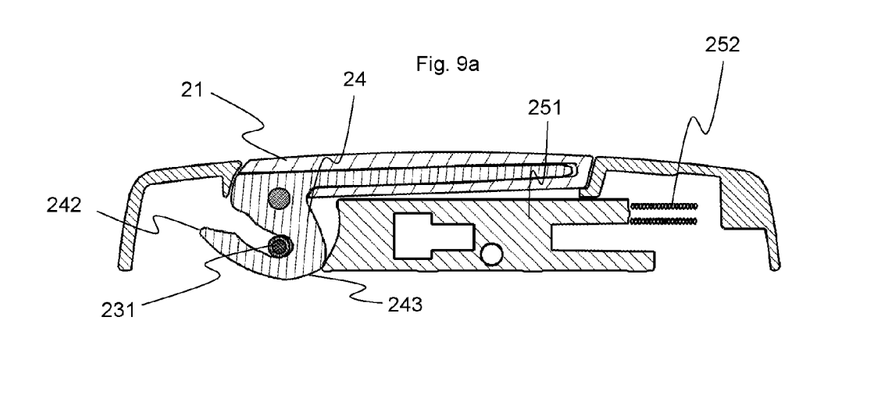
FIG. 9 views similar to FIG. 6, with the lever all the way down.
Figure 9B:
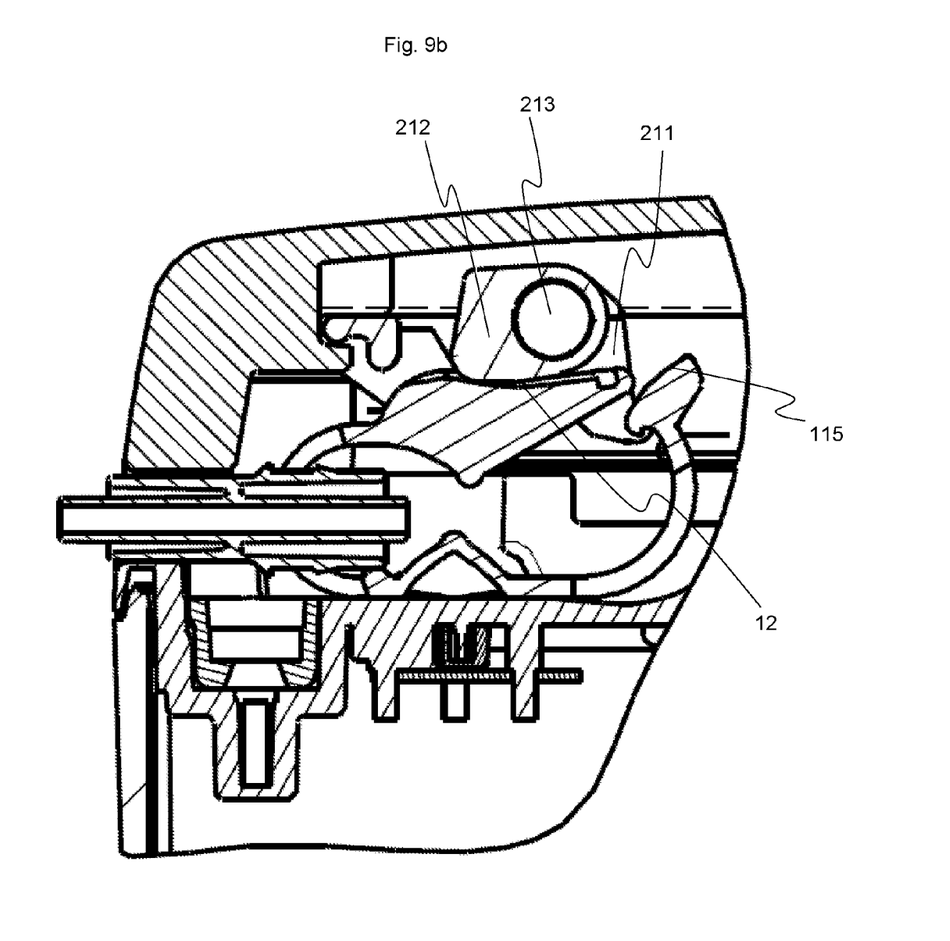

While continuing the movement of closing down the lever (21), the pressure being applied by the back cam (212) to the back (12) is released, this branch rises back up to the open position, and lastly, the pressure applied to the actuation element (115) is released. Finally, the pair of head cams (211) moves past the actuation element (115) and slides under the free end of the head (111). The lever (21) is now all the way down, the clamp (10) is open, and the door (22) is closed and locked into this position by the hook (24). FIG. 9 illustrate this situation.

If the lever (21) is now lifted, the pair of head cams (211) will first move the head end (111) away to make enough room for the other end (121) to go through. The back cam presses on the back (12) until its end (121) has gone by in front of the pulled-back end of the head (111), which is still held by the pair of head cams (211). The pair of head cams (211) then stops pressing on the actuation element (115) and the end of the head (111) returns to its normal position. Finally, the back cam (212) stops pressing on the back (12), which comes back up until its end (121) comes up against the end of the head, with the tab (112) going into the recess (122). The hook (24) is no longer hooked into the roller (231), and the door can be opened. The clamp (10) is closed again.

Figure 10:
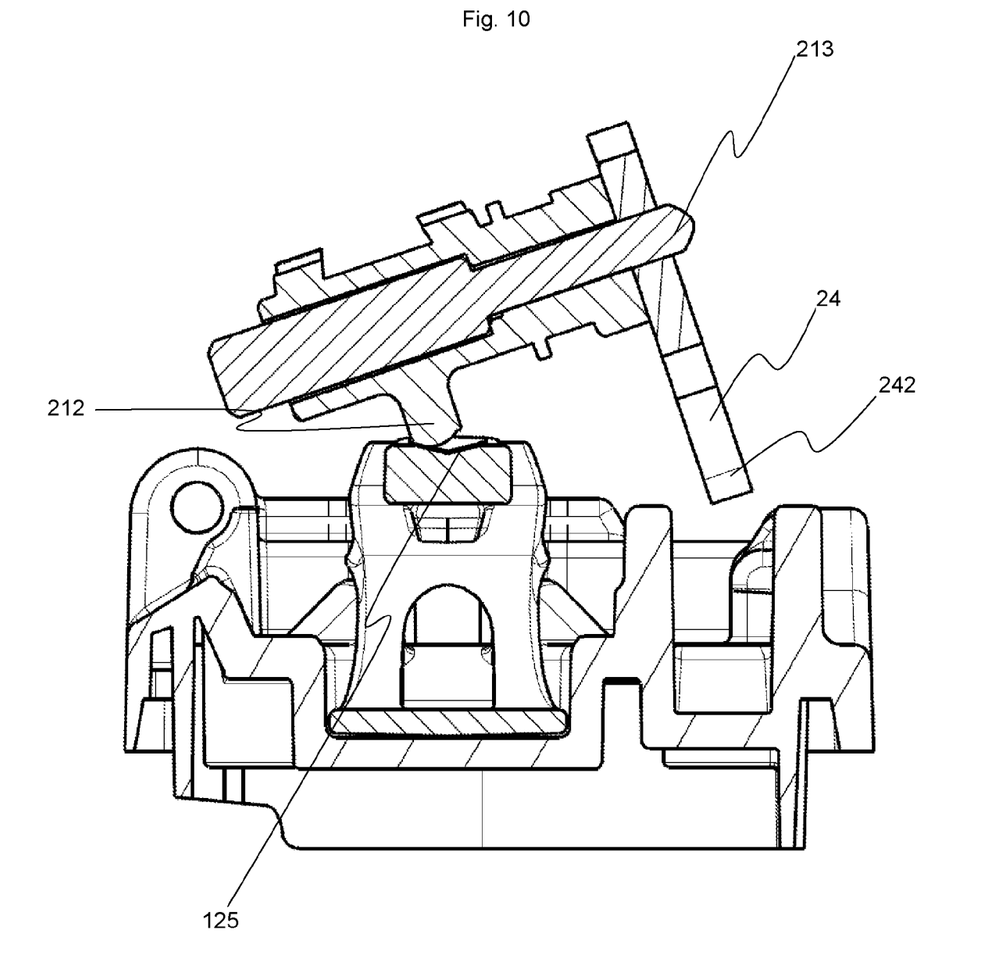
FIG. 10 cross-section view of the door and the upper face of the pump housing at the moment when the unlocking means make contact with the back of the clamp while the door is being shut.

In order to guide the back cam (212), it is preferable to provide the back (12) of the clamp with a guide groove (125). This keeps the back (12) of the clamp from sliding and going askew when the back cam (212) presses on it. FIG. 10 shows this cooperation.

In order to keep the door from being opened by some unintentional movement, a return device (25) is provided in the door (22). This return device (25) is essentially made up of a mobile plate (251) that is pushed against the outer face of the hook (24) by a spring (252). This plate (251) can move translationally against the action of the spring (252) if the lever (21) is raised. As long as the lever (21) has not gone past a certain point in its lifting movement, the plate (251) presses against the outer face of the bottom (243) of the hook (24) and forces the lever (21) to return to the closed down position against the door (22). The point of no return corresponds to the moment where the head cams (211), which are initially underneath the head (11), leave the end of the head (111) to go over the actuation element (115) of the head. In other words, as long as this point of no return has not been reached, the clamp (10) is still open, the hook (24) is still engaged with the roller (231) and the door (22) is closed down. The mobile plate (251) is equipped with pins (253) that fit in under stops (234) placed on the pump housing (23) when the plate moves translationally in response to the spring action. The door (22) is therefore not only locked by the hook (24) engaged with the roller (231), but also by the pins (253) held in place by the stops (234).

Moreover, sensors (232) can be placed at the stops (234) in order to detect the right position of the pins (253), indicating that the door is closed right. The signal provided by the detector can be used to control the pump (20).

In order to get the clamp (10) positioned right in the pump (20), the clamp (10) is equipped with wings for positioning (14) that fit into receptacles provided for this purpose in the housing (23). The shape of the clamp (10) and of the corresponding receptacle (235) prohibit the tube from being positioned the wrong way in the pump.

It is additionally preferable to immobilize the clamp (10) in the pump. For this purpose, an insert (15) is placed in the opening (134) located in the U-shaped bottom of the clamp. This insert (15) has a circular groove (151) on its periphery. The opening (134) has a circular cut-out (135) in the continuation of the tube that fits around the groove (151), with the length of the cut-out corresponding substantially to the width of the groove (151). In this way, the insert is translationally blocked in the opening (134) so that it cannot move with respect to the clamp (10) in the longitudinal direction of the tube nor along the opening (134). However, it can tilt slightly around a pivot axis going through the cut-outs (135) in the opening (134), which lends the tube/clamp assembly a certain amount of flexibility.

This insert (15), preferably of cylindrical-shaped hard plastic material, protects the end of the flexible tube coming out of the clamp (10).

The insert (15) has end fittings (152, 153) extending from both ends of the groove (151). Tubes with different characteristics can be attached to these end fittings (152, 153).

Figure 11A:
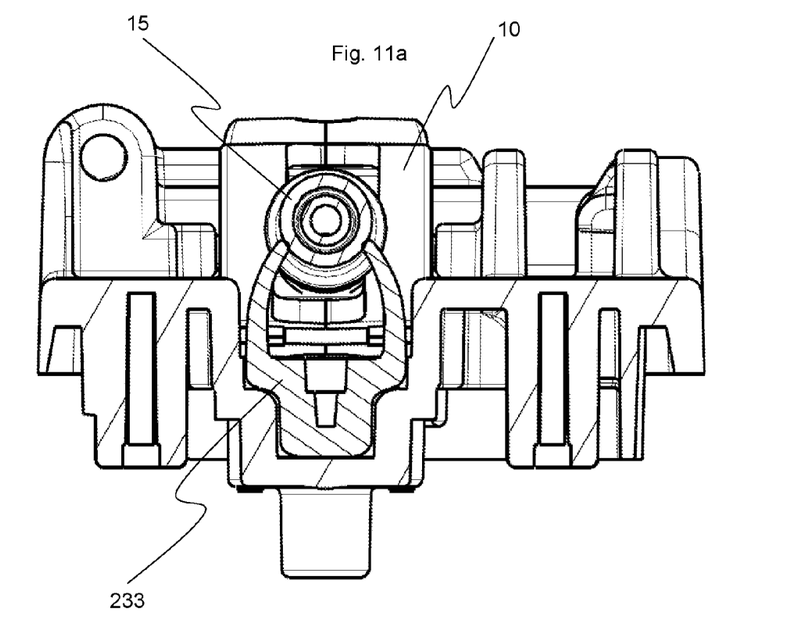
Figure 11B:
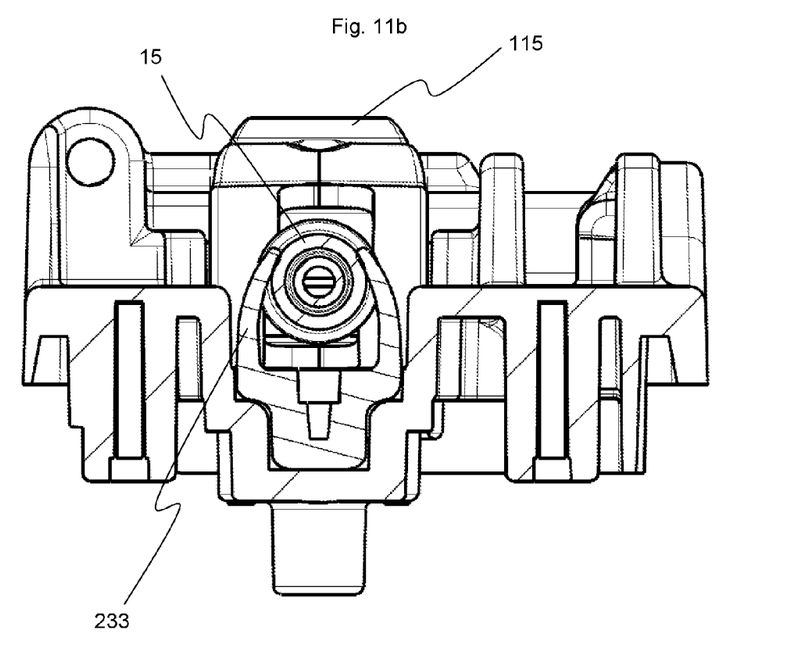

The outer end fitting (152) can cooperate with an insert support (233) placed on the pump housing (23). This support (233) is a cylindrical channel into which the outer end fitting (152) can be snapped. This snapping in makes a "click" when the clamp is installed in the housing. If the clamp is ever inserted incompletely into its receptacle, and the outer end fitting (152) is not correctly snapped into its support (233), there is a ridge provided in the door that will come to bear on the outer end fitting (152) when the door (22) is closed, until it is correctly snapped into its support (233). This way, the clamp will be correctly immobilized in the pump when the door is first locked, at the latest.

REFERENCES

10 Clamp
11 Clamp head
11' Lower branch of the clamp
111 Head end
112 Tab
113 Protrusion
114 Opening
115 Actuation element
12 Upper branch (back)
121 End of back
122 Recess
123 Protrusion
125 Guide groove
13 Bottom
134 Bottom opening
135 Insert cut-out
14 Wings for positioning
15 Insert
151 Groove
152 Outer end fitting
153 Inner end fitting
20 Pump
21 Lever
211 Pair of head cams
212 Back cam
213 Rotation shaft
22 Door
23 The part of the housing covered by the door when the latter is closed
231 Roller
232 Sensor
233 Insert support
234 Stops for pins
235 Clamp receptacle
24 Hook
241 Hook base
242 Hook tip
243 Bottom of hook
25 Return device
251 Mobile plate
252 Spring
253 Pins

The invention claimed is:

1. Pump for perfusion comprising:
a flexible tube equipped with a clamp that can be opened and closed, wherein the clamp is located inside the pump wherein said clamp comprises:
 a substantially U-shaped band of plastic material, with a free end of a first branch of the U-shaped band bent toward a free end of a second branch of the U-shaped band, called the back, to form the head of the clamp, so that in the closed position, the free end of the back, called the back end, is supported under the free end of the head, called the head end, wherein a surface of the head end overlaps a surface of the back end, whereas in the open position, the back end is above the head end at a distance,
 a pair of openings spaced so as to accommodate a flexible tube going through the clamp and supported by the clamp, and two opposite protrusions to seal off the flexible tube by compressing the flexible tube when the clamp is in the closed position,
 means for moving the head end away from the back end in an opening direction parallel to the surfaces where the head end and the back end overlap, by exerting pressure on the head end in the opening direction parallel to the surfaces where the head end and the back end overlap in order to open the clamp when the clamp is in the closed position, and
 means for locking the head end on the back end in the closed position so as to prevent the head end from moving away from the back end in the opening direction parallel to the surfaces where the head end and the back end overlap, when pressure is exerted only on the head end, and to permit the head end to move in the opening direction parallel to the surfaces where the head end and the back end overlap only after the back end has been moved down from the closed position,
a door that can be opened and closed in order to place or take out a flexible tube equipped with a clamp, and means for opening or closing the clamp comprising a pivoting lever equipped with at least one head cam to move the head end away from the back end of the clamp, wherein the lever is equipped with means for unlocking the locking means of the clamp, wherein the lever is additionally equipped with a hook able to cooperate with a roller located on the pump housing in order to keep the door closed, and wherein the door is equipped with a return element that serves to move the hook into the closed position as soon as the clamp opening and closing means have placed the clamp in the open position.

2. Pump according to claim 1, wherein the locking means comprises a tab located on the head end and a recess located on the back end, the tab and the recess being arranged so that in the closed position of the clamp, the tab goes into the recess.

3. Pump according to claim 1, wherein an insert is provided in one of the openings of the clamp to receive the end of the flexible tube, the insert being integral with the clamp.

4. Pump according to claim 3, wherein the insert is equipped with an end fitting for attaching another flexible tube.

5. Pump according to claim 3, wherein the insert is provided with a groove on its outer circumference, the two opposite edges of the clamp opening being received in this groove.

6. Pump according to claim 1, wherein a longitudinal groove is provided on the outer face of the back.

7. Pump according to claim 1, which is equipped with means for closing the clamp when the door is opened.

8. Pump according to claim 1, wherein the unlocking means consist of a back cam, the head cam and the back cam being disposed on the lever pivot shaft so that when the lever is actuated to open the clamp, first the back cam presses on the back of the clamp until the clamp locking means are unlocked and the back cam holds the clamp in this position, then the head cam moves the head end far enough away from the back end to leave room for the back end to move up from the closed position to the open position, after which the back cam releases the pressure on the back of the clamp, and lastly, the head cam releases the end of the head.

9. Pump according to claim 1, wherein the lever is placed in the door of the pump.

10. Pump according to claim 1, wherein a support is provided on the pump housing for snapping in a clamp insert provided in one of the openings of a clamp to receive an end of a flexible tube.

11. Combination of a pump for perfusion according to claim 1 and a flexible tube set for perfusion passing through the clamp.

12. Pump for perfusion comprising:

a door that can be opened and closed in order to place or take out a flexible tube equipped with a clamp, means for opening or closing a clamp comprising a pivoting lever equipped with at least one head cam to move a head end away from a back end of a clamp located inside the pump, wherein the lever is equipped with means for unlocking the locking means of the clamp, wherein the lever is additionally equipped with a hook able to cooperate with a roller located on the pump housing in order to keep the door closed, and wherein the door is equipped with a return element that serves to move the hook into the closed position as soon as the clamp opening and closing means have placed the clamp in the open position.

13. Pump according to claim 12, which is equipped with means for closing the clamp when the door is opened.

14. Pump according to claim 12, wherein the unlocking means consist of a back cam, the head cam and the back cam being disposed on the lever pivot shaft so that when the lever is actuated to open the clamp, first the back cam presses on the back of the clamp until the clamp locking means are unlocked and the back cam holds the clamp in this position, then the head cam moves the head end far enough away from the back end to leave room for the back to go through back end to move up from the closed position to the open position, after which the back cam releases the pressure on the back of the clamp, and lastly, the head cam releases the end of the head.

15. Pump according to claim 12, wherein the lever is placed in the door of the pump.

16. Pump according to claim 1, wherein the protrusions are staggered along a direction from one of the orifices to the other in the closed position of the clamp, so that the back can be pushed toward the bottom past the closed position of the clamp.

17. Pump according to claim 2, wherein an actuation element is provided on the end of the head.

18. Pump according to claim 1, wherein the locking means comprises a tab located on one of the head end and the back end and a recess located on the other of the head end and the back end, the tab and the recess being arranged so that in the closed position of the clamp, the tab goes into the recess.

* * * * *